(12) United States Patent
Ahn et al.

(10) Patent No.: US 10,799,198 B2
(45) Date of Patent: Oct. 13, 2020

(54) X-RAY IMAGE CAPTURE APPARATUS

(71) Applicants: VATECH Co., Ltd., Gyeonggi-do (KR); VATECH EWOO Holdings Co., Ltd., Gyeonggi-do (KR)

(72) Inventors: Byung-Jun Ahn, Gyeonggi-do (KR); Sang-Og Na, Gyeonggi-do (KR); Yong-Joo Yang, Gyeonggi-do (KR); Sung-Il Choi, Gyeonggi-do (KR); Dae-Ki Hong, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 132 days.

(21) Appl. No.: 15/771,394

(22) PCT Filed: Oct. 26, 2016

(86) PCT No.: PCT/KR2016/012045
§ 371 (c)(1),
(2) Date: Apr. 26, 2018

(87) PCT Pub. No.: WO2017/073997
PCT Pub. Date: May 4, 2017

(65) Prior Publication Data
US 2018/0310898 A1   Nov. 1, 2018

(30) Foreign Application Priority Data

Oct. 26, 2015   (KR) .................. 10-2015-0149018

(51) Int. Cl.
*A61B 6/14*    (2006.01)
*A61B 6/00*    (2006.01)
(Continued)

(52) U.S. Cl.
CPC .............. *A61B 6/14* (2013.01); *A61B 6/00* (2013.01); *A61B 6/02* (2013.01); *A61B 6/032* (2013.01);
(Continued)

(58) Field of Classification Search
CPC .... A61B 6/00; A61B 6/02; A61B 6/14; A61B 6/4035; A61B 6/42; A61B 6/52;
(Continued)

(56) References Cited

U.S. PATENT DOCUMENTS 4,286,162 A * 8/1981 Suzuki ..................... A61B 6/14
378/40
4,783,793 A * 11/1988 Virta ........................ A61B 6/14
378/39
(Continued)

FOREIGN PATENT DOCUMENTS

JP   2001-346796 A   12/2001
JP   2006-314774 A   11/2006
(Continued)

OTHER PUBLICATIONS

Korean Intellectual Property Office, International Search Report of International Application No. PCT/KR2016/012045, dated Feb. 13, 2017.
(Continued)

*Primary Examiner* — Jurie Yun
(74) *Attorney, Agent, or Firm* — IP Legal Services, LLC (57) ABSTRACT

Disclosed is an X-ray image radiographing apparatus being economical by using a small width sensor, occupying less space, and providing an X-ray CT image and an X-ray panoramic image without distortion and with high accuracy. An X-ray image radiographing apparatus according the present invention includes a rotation supporter rotating based on a rotation shaft; a generating unit including an (Continued)

X-ray generator radiating an X-ray beam; a sensing unit including a small width sensor moving in a width direction thereof; and a controller changing a rotation speed of the rotation supporter or a frame rate of the sensing unit to compensate changes in magnification ratio according to a distance change between an area of interest of the subject and the small width sensor when performing an X-ray image radiographing sequence obtaining a number of CT images by rotating the rotation supporter.

9 Claims, 6 Drawing Sheets (51) Int. Cl.
*A61B 6/03* (2006.01)
*A61B 6/06* (2006.01)
*A61B 6/02* (2006.01)
*G01N 23/046* (2018.01)

(52) U.S. Cl.
CPC ............... *A61B 6/06* (2013.01); *A61B 6/405* (2013.01); *A61B 6/4035* (2013.01); *A61B 6/42* (2013.01); *A61B 6/4435* (2013.01); *A61B 6/4452* (2013.01); *A61B 6/469* (2013.01); *A61B 6/52* (2013.01); *A61B 6/5258* (2013.01); *A61B 6/54* (2013.01); *A61B 6/542* (2013.01); *G01N 23/046* (2013.01)

(58) Field of Classification Search
CPC ........... A61B 6/54; A61B 6/469; A61B 6/032; A61B 6/06; A61B 6/4208; A61B 6/542; A61B 6/4435; A61B 6/4441; A61B 6/58; G01N 23/046

USPC ... 378/4, 38, 39, 40, 116, 98.5, 207, 901, 20
See application file for complete search history.

(56) References Cited

U.S. PATENT DOCUMENTS

| | | |
|---|---|---|
| 5,511,106 A | 4/1996 | Doebert et al. |
| 2009/0041191 A1 | 2/2009 | Suzuki et al. |
| 2012/0183120 A1 | 7/2012 | Tomoe |
| 2012/0300895 A1 | 11/2012 | Koivisto et al. |
| 2012/0300900 A1 | 11/2012 | Koivisto et al. |
| 2013/0170610 A1* | 7/2013 | Arai .................. A61B 6/06 378/4 |
| 2014/0193768 A1 | 7/2014 | Ogawa et al. |
| 2015/0289827 A1 | 10/2015 | Laukkanen et al. |
| 2016/0174916 A1 | 6/2016 | Nyholm et al. |
| 2017/0000432 A1 | 1/2017 | Lim et al. |
| 2017/0265744 A1 | 9/2017 | Nyholm et al. |

FOREIGN PATENT DOCUMENTS

| | | |
|---|---|---|
| JP | 2011-067550 A | 4/2011 |
| KR | 10-2009-0078646 A | 7/2009 |
| KR | 10-2010-0120815 A | 11/2010 |
| KR | 10-2012-0114392 A | 10/2012 |
| KR | 10-1396663 B1 | 5/2014 |
| KR | 10-2015-0061684 A | 6/2015 |
| KR | 10-2015-0102989 A | 9/2015 |
| KR | 10-2015-0106709 A | 9/2015 |

OTHER PUBLICATIONS

Korean Intellectual Property Office, Written Opinion of International Application No. PCT/KR2016/012045, dated Feb. 13, 2017.
European Patent Office, European Search Report of corresponding EP Patent Application No. 16860180.5, dated Jun. 11, 2019.

* cited by examiner

X-RAY IMAGE CAPTURE APPARATUS

CROSS REFERENCE TO RELATED APPLICATIONS

This application is a National Stage Patent Application of PCT International Patent Application No. PCT/KR2016/012045 (filed on Oct. 26, 2016) under 35 U.S.C. § 371, which claims priority to Korean Patent Application No. 10-2015-0149018 (filed on Oct. 26, 2015), the teachings of which are incorporated herein in their entireties by reference.

TECHNICAL FIELD

The present invention relates to an X-ray imaging apparatus. More particularly, the present invention relates to an X-ray imaging apparatus capable of providing a CT image and a panoramic image by using a sensor with a narrow width while using a low dose of X-rays.

BACKGROUND ART

In the medical field, an X-ray radiographing apparatus refers to an apparatus that radiates a predetermined amount X-rays toward a body part to be radiographed, senses the X-rays having passed therethrough by using an X-ray sensor, and reconstructs an X-ray image by using electrical signals sensed by the X-ray sensor. The X-rays having passed through the body part are attenuated a rate varying according to substances in their travelling path and are transformed to electrical signals by the X-ray sensor by photoelectric. The X-ray radiographing apparatus provides information of interior of the radiographing target in an X-ray image by using electrical signals in which accumulated attenuation rate is reflected according to the X-ray travelling path.

In the field of dental diagnosing, CT images are widely used as the CT images accurately and clearly display a three-dimensional X-ray image of the teeth arrangement, temporomandibular joint or head of the patient, which are main parts of interest among body parts, and tomographic images according to the position and direction desired by the user. Accordingly, such images are used in fields requiring high precision such as implant treatment. An X-ray computed tomography (CT) radiographing apparatus reconstructs X-ray images of a radiographing target which are radiographed in various angles, and provides a three-dimensional X-ray image of the radiographing target. For this, the X-ray CT radiographing apparatus includes an X-ray generator, an X-ray sensor disposed to face the X-ray generator with a subject disposed therebetween, a rotation supporter rotating the X-ray generator and the X-ray sensor while supporting the same, and an image reconstructing unit implementing a CT image by using results sensed by the X-ray sensor.

In order to obtain an X-ray CT image, the X-ray generator and the X-ray sensor rotates facing each other within a predetermined angular range based on a rotation shaft passing through the radiographing target, and X-ray CT data of a field of view in various angles, that is a FOV, is obtained. When performing general X-ray CT radiographing, the X-ray generator and the X-ray sensor rotates based on a rotation shaft that is the central axis of the FOV, and X-rays having passed the entire area of the FOV are received in various angles. Accordingly, for panoramic X-ray imaging, a large-size sensor is significantly larger than the X-ray sensor is required. However, when a size of the X-ray sensor increases, manufacturing cost thereof also increases, thus in the field of a dental X-ray imaging apparatuses, a method of radiographing a CT image using a small width sensor of a large FOV that is twice larger than a width of the small width sensor is required.

Meanwhile, in the dental field, an X-ray panoramic image has been widely used for a long time and is recognized as a standard image indispensable for diagnosing. Accordingly, in a radiographing apparatus for providing an X-ray CT image, a function of panoramic imaging is frequently added. Herein, it is required to provide an X-ray panoramic image with high accuracy since the image is important in diagnosis.

DISCLOSURE

Technical Problem

Accordingly, the present invention has been made keeping in mind the above problems occurring in the prior art, and an object of the present invention is to provide an X-ray imaging apparatus which is economical by using a small width sensor, occupies less space for installing and radiographing, provides an X-ray CT image of a relatively wide FOV, and effectively provides an X-ray panoramic image without distortion and with high accuracy.

Technical Solution

In order to accomplish the above object, an X-ray imaging apparatus according to one aspect of the present invention includes: a rotation supporter rotating based on a rotation shaft; a generating unit disposed in a first side of the rotation supporter and including an X-ray generator radiating an X-ray beam; a sensing unit disposed in a second side of the rotation supporter to face to the generating unit with a subject in between, and including a small width sensor moving in a width direction thereof and perpendicular to the rotation shaft when the rotation supporter rotates; and a controller changing a rotation speed of the rotation supporter or a frame rate of the sensing unit when performing an X-ray imaging sequence obtaining a number of transmitted images by rotating the rotation supporter.

The controller may compensate a change in magnification ratio by changing the rotation speed of the rotation supporter or the frame rate of the sensing unit according to a change in distance between an area of interest of the subject and the small width sensor.

The controller may relatively increase the rotation speed of the rotation supporter or relatively decrease the frame rate of the sensing unit in a section where the magnification ratio is relatively large.

Herein, the controller may maintain the rotation speed of the rotation supporter to be constant, and relatively decrease the frame rate of the sensing unit in a section wherein the magnification ratio is relatively large.

The X-ray imaging sequence may be a panoramic imaging sequence, and an area of interest of the subject may be distributed along an arch trajectory Herein, the controller may relatively increase the rotation speed of the rotation supporter or relatively decreases the frame rate of the sensing unit in a section for obtaining a transmitted image of posterior teeth than in a section for obtaining a transmitted image of anterior teeth.

In addition, the apparatus may further include an image reconstructing unit shifting and overlapping the number of transmitted images in a predetermined interval to compensate a magnification ratio difference in a horizontal axial direction according to a position on the arch trajectory, and correcting a magnification ratio in a longitudinal axial direction by applying ratios different from each other according to a position in a horizontal axial direction on the arch trajectory.

An X-ray imaging apparatus according to another aspect of the present invention includes: a rotation supporter rotating based on a rotation shaft; a generating unit disposed in a first side of the rotation supporter and including an X-ray generator radiating an X-ray beam; a sensing unit disposed in a second side of the rotation supporter to face the generating unit with a subject in between, and including a small width sensor moving in a width direction thereof and perpendicular to the rotation shaft when the rotation supporter rotates; and a controller changing a rotation speed of the rotation supporter or a frame rate of the sensing unit to compensate a change in magnification ratio according to a change in distance between an area of interest of the subject and the small width sensor when performing an X-ray imaging sequence obtaining a number of transmitted images by rotating the rotation supporter, wherein the X-ray generator is installed such that a direction of the X-ray beam has a predetermined slope relative to a surface perpendicular to the rotation shaft, and the small width sensor is installed to be inclined at a predetermined angle relative to a surface parallel to the rotation shaft.

Herein, the X-ray imaging sequence may be a panoramic imaging sequence, and the area of interest of the subject may be distributed along an arch trajectory, and the apparatus may further include an image reconstructing unit compensating a magnification ratio difference in a horizontal axial direction according to a position on the arch trajectory by shifting and overlapping the number of transmitted images in a predetermined interval, and correcting a magnification ratio in a longitudinal axial direction by applying ratios different from each other according to a position in a horizontal axial direction on the arch trajectory.

The image reconstructing unit may correct upper and low magnification ratio differences due to tilting of the small width sensor.

Advantageous Effects

An X-ray imaging apparatus to which a configuration according to the present invention is applied can be economical by using a small width sensor, occupy less space for installing and radiographing, provide an X-ray CT image of a relatively wide FOV, and effectively provide an X-ray panoramic image without distortion and with high accuracy.

DESCRIPTION OF DRAWINGS

FIGS. 5 (a) and (b) are views schematically showing an optimal relation between an arch shape and a panoramic imaging the same.

FIG. 6 (a), (b), (c), and (d) are views schematically showing distortion of a panoramic imaging the arch shape of FIGS. 5(a) and (b), and a correct method thereof.

MODE FOR INVENTION

Hereinbelow, exemplary embodiments of the present invention will be described in detail with reference to the accompanying drawings. The embodiments set forth herein are provided for illustrative purposes to fully convey the concept of the present invention. It will be apparent to a person skilled in the art that the present invention should not be construed to be limited to these embodiments. Throughout the drawings, the same reference numerals will refer to the same or like parts. Descriptions of some components depicted in a specific drawing will be omitted, when their reference numerals are identical to those of the components described with reference to another drawing.

Figure 1:
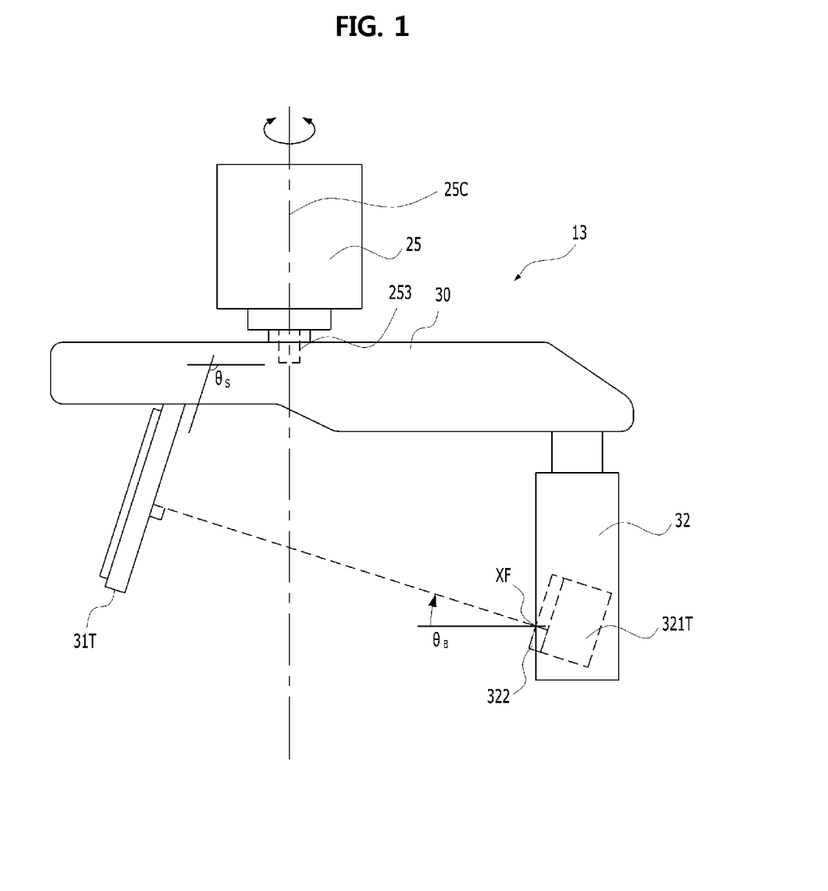
FIG. 1 is a view showing a configuration of a radiographing unit of an X-ray imaging apparatus according to an embodiment of the present invention FIGS. 2 (a) and (b) are views showing a principle of scaling down a rotation range of the radiographing unit on the assumption that a FOV having the same size is provided by the configuration of the radiographing unit according to an embodiment of FIG. 1.

FIG. 1 is a view showing a configuration of a radiographing unit of an X-ray imaging apparatus according to an embodiment of the present invention.

An X-ray imaging apparatus according to the present invention is configured to include a radiographing unit obtaining a number of X-ray transmitted images, a controller controlling the radiographing unit, and a reconstructing unit reconstructing an X-ray CT image and a panoramic image by using the number of X-ray transmitted images. If necessary, a radiographing casing may be further included to cover the exterior of the radiographing unit. The present figure shows a configuration of the radiographing unit.

The radiographing unit 13 includes a rotation driver 25, and a rotation supporter 30 rotating based on a rotation shaft 25C by the rotation driver 25, a generating unit 32 disposed in a first side of the rotation supporter 30 and including X-ray generator 321T and a collimator 322 so as to radiate an X-ray beam collimated in a predetermined width, and a sensing unit 31T disposed in a second side of the rotation supporter 30 to face the generating unit 32 with a subject in between, and including a small width sensor moving in a direction to where the rotation supporter 30 rotates. Preferably, the small width sensor moves in a tangential direction of a rotation trajectory.

In terms of the X-ray generator 321T and the collimator 322, the X-ray generator 321T and the collimator 322 are installed such that a radiation direction of an X-ray beam shown in a dotted line has a predetermined slope $\theta_B$ relative to a surface perpendicular to the rotation shaft 25C of the rotation supporter 30. The sensing unit 31T includes the small width sensor facing the X-ray generator 321T such that a light receiving surface thereof is inclined at a predetermined angle relative to a surface that is parallel to the rotation shaft 25C. Herein, the radiation direction of the X-ray beam is upwardly inclined relative to a surface perpendicular to the rotation shaft 25C so that the predetermined slope $\theta_B$ is 0 degrees<$\theta_B$<90 degrees. More preferably, the predetermined slope $\theta_B$ may satisfy a condition to be 0 degrees<$\theta_B$<45 degrees. Accordingly, the sensing unit 31T is downwardly inclined relative to a surface parallel to the rotation shaft 25C, that is an outer circumferential surface of a virtual cylindrical form based on the rotation shaft 25C, at an angle corresponding to the $\theta_B$ so that an angle $\theta_S$ between the sensing unit 31T and a surface to which the rotation supporter 30 belongs is 90 degrees<$\theta_S$<180 degrees. More preferably, the angle $\theta_S$ may satisfy a condition to be 90 degrees<$\theta_S$<135 degrees. It is preferable for the sensing unit 31T to form an angle relative to the radiation direction of the X-ray beam starting from a focal point XF of the X-ray generator 321T to be perpendicular to when viewed from the side.

The radiation direction of the X-ray beam is upwardly inclined and the sensing unit 31T is downwardly inclined so that an examinee may easily put his or her head therein since the space inside the radiographing unit is formed in a conical shape where the bottom part is wider.

Meanwhile, in the present embodiment, a housing of the generating unit 32 is disposed perpendicular to the rotation supporter 30, and the X-ray generator 321T is disposed to be inclined therein, but the generating unit 32 itself may be disposed to be approximately parallel to the sensing unit 31T.

The rotation driver 25 is supported by an upper interior part of the radiographing casing, and installed to be connected to the rotation shaft 25C of the rotation supporter 30 at a driving shaft 253 thereof. In an example, the rotation driver 25 may include a direct drive (DD) motor, and may be configured such that the center of the driving shaft 253 of the DD motor to be identical to the rotation shaft 25C of the rotation supporter 30. Herein, power wirings or signal wirings around the driving shaft 253 may be connected by using a slip ring to prevent cables from being twisted. The slip ring may be a wireless slip ring having non-contacting point.

Figure 2:
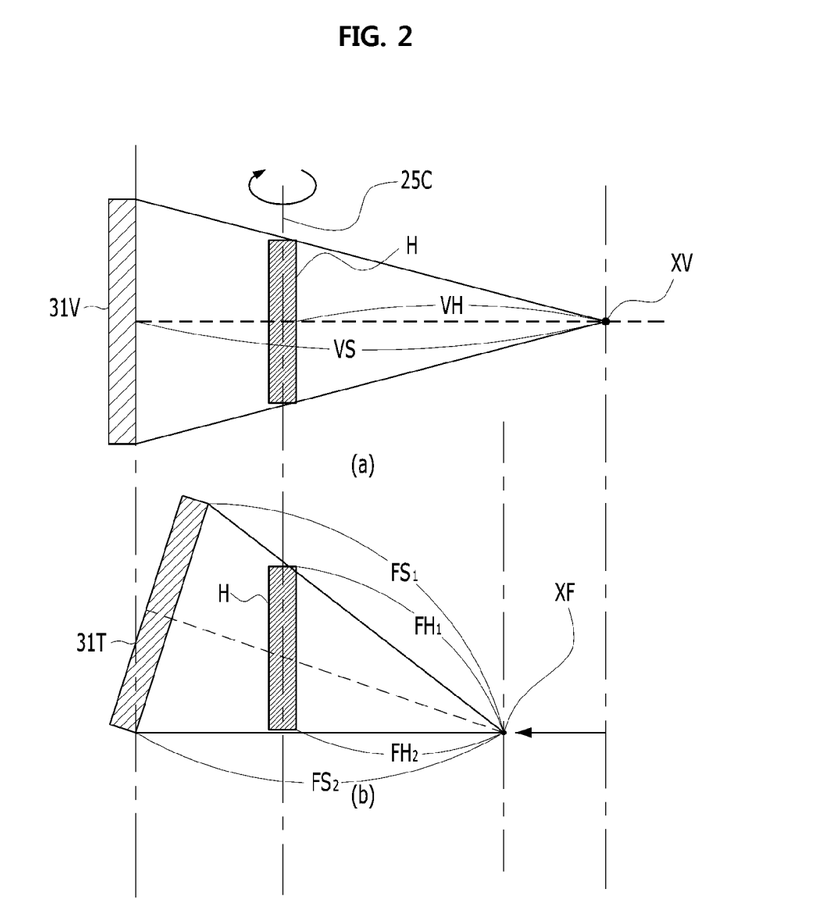
FIG. 2(a) shows a case where a radiation direction of an X-ray beam is parallel to a surface perpendicular to a rotation shaft as a typical case.
FIG. 2(b) shows a case where a sensing unit and the radiation direction of the X-ray beam are inclined.

FIG. 2 is a view showing a principle of scaling down a rotation range of the radiographing unit on the assumption that a FOV having the same size is provided by the configuration of the radiographing unit according to an embodiment of FIG. 1

FIG. 2(a) shows a case where a radiation direction of an X-ray beam is parallel to a surface perpendicular to a rotation shaft 25C as a conventional case, and thus a sensing unit 31V is parallel to the rotation shaft 25C, and FIG. 2(b) shows a case where the sensing unit 31T and the radiation direction of the X-ray beam according to the present invention are inclined as described above with reference to FIG. 2.

Herein, a height H of a FOV is identical in FIGS. 2(a) and 2(b). In FIG. 2(b), an X-ray beam is obliquely irradiated, and the sensing unit 31T is installed to be inclined so that a focal point XF of the X-ray beam is positioned close to the rotation shaft 25C which is relatively closer than a focal point XV in FIG. 2(a). This means that a rotation radius of the radiographing unit may be narrowed by a distance between the focal points XF and XV. Accordingly, a space occupied by the X-ray imaging apparatus may be reduced, more specifically, a size of the radiographing casing described above may be reduced.

Meanwhile, in FIG. 2(a), a magnification ratio is defined by a distance between from a focal point XV of an X-ray beam for a distance between the focal point XV of the X-ray beam and the subject, to the sensing unit 31V. In the figure, except for an error coming from the sensor unit 31V which is symmetrical in the upper and lower parts based on a horizontal line, and the subject not being a spherical form, the magnification ratios for the upper and low parts of the sensing unit 31V are approximately identical. However, in FIG. 2(b), since the sensing unit 31T is disposed to be inclined in a longitudinal axis of the subject, a distance between the upper part of the subject and the upper part of the sensing unit 31T is relatively closer than a distance between the low part of the subject and the low part of the sensing unit 31T. In the figure, $FS_1=FS_2$ and $FH_1>FH_2$, and thus a magnification ratio of an image of the upper part of the subject, that is $FS_1/FH_1$, is relatively smaller than a magnification ratio of an image of the low part of the subject, that is, $FS_2/FH_2$. Accordingly, when an X-ray transmitted image is radiographed by using the radiographing unit 13 of FIG. 1, for example, an image of the subject with a square form becomes distorted as a trapezoid form.

Accordingly, the X-ray imaging apparatus according to the present invention corrects a difference by expanding the upper and low parts according to a slope of the sensor when the X-ray imaging apparatus reconstructs and provides an X-ray transmitted image or a panoramic image. When the reconstructing unit reconstructs and provides a panoramic image by using a number of transmitted images obtained according to an arch trajectory, the reconstructing unit reconstructs a primary panoramic image by shifting and overlapping the number of transmitted images in a predetermined interval in a horizontal direction, and provides a panoramic image in which distortion is corrected by reflecting a magnification ratio difference of the upper and low directions in the primary panoramic image.

Figure 3:
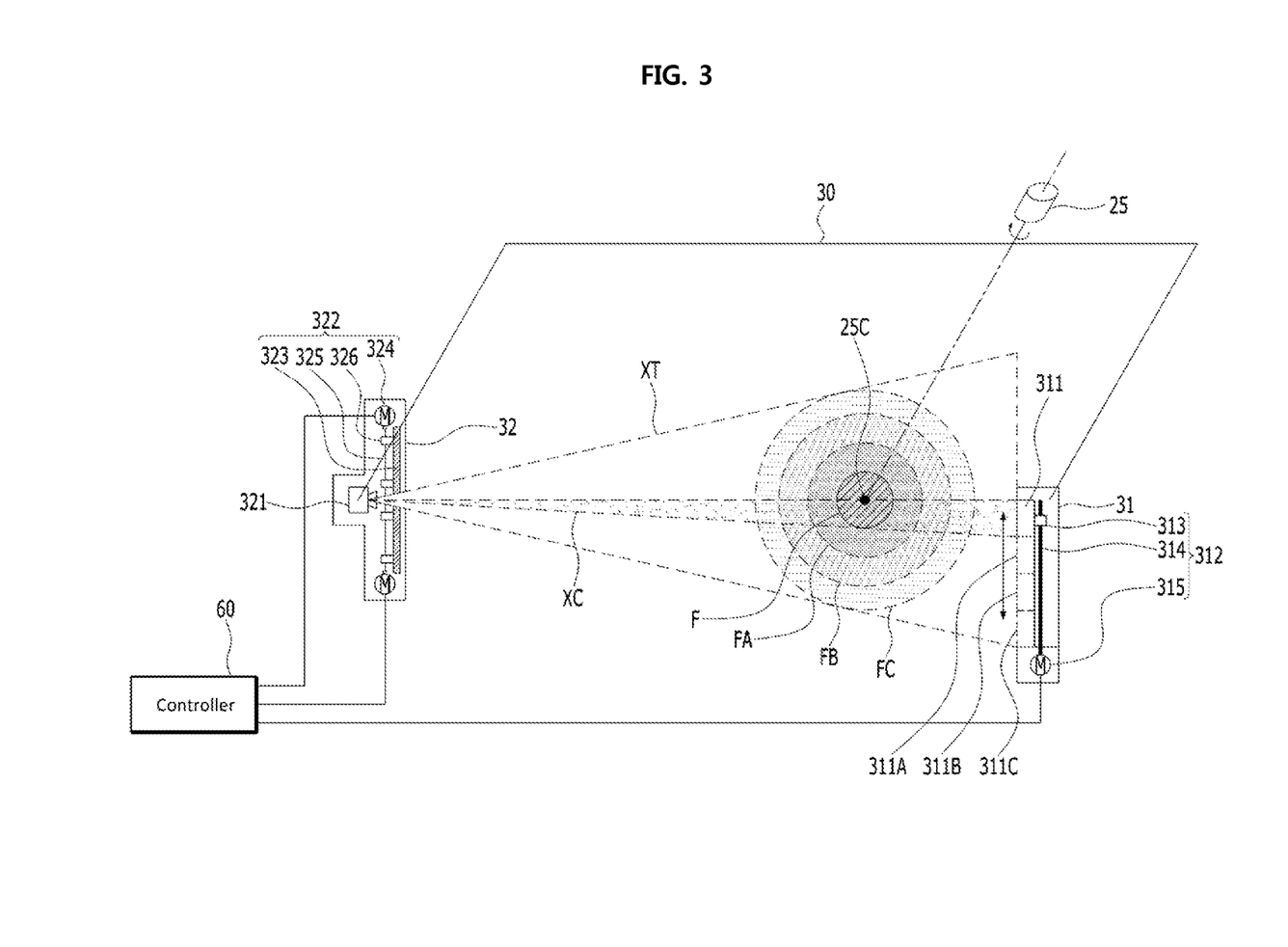
FIG. 3 is a view showing a configuration of the X-ray imaging apparatus according to an embodiment of the present invention.

FIG. 3 is a view showing a configuration of providing a wide FOB by using the small width sensor in the radiographing unit of the X-ray imaging apparatus according to an embodiment of the present invention.

The present figure shows a configuration of the radiographing unit that obtains a number of X-ray transmitted images by rotating the rotation supporter 30 and simultaneously moving the small width sensor 311 when performing a radiographing sequence, and the present figure schematically shows a rotation shaft 25C of the rotation supporter 30 described above when viewed from above. The radiographing unit performs an X-ray imaging sequence by receiving a control signal from the controller 60. In a dental X-ray imaging apparatus, an X-ray imaging sequence may be classified into an X-ray CT radiographing sequence and a panoramic imaging sequence. Herein, the X-ray CT radiographing sequence will be described as an example first.

When performing the X-ray CT radiographing sequence, a radiation path of an X-ray beam partially passing through a subject is rotated, at the same time, a virtual X-ray beam center is moved so that the X-ray beam is irradiated on all parts within a FOV in various angles and in a predetermined range or more The sensing unit 31 includes the narrow X-ray sensor 311 facing to the generating unit 32. Herein, when the total height and width of a FOV of a CT image to be obtained are respectively t1 and w1 (herein, height refers to a maximum size in a direction parallel to a rotation shaft, width refers to a maximum size in a direction perpendicular to the rotation shaft), a height t2 of the narrow X-ray sensor is equal to or greater than expansion rate*first height (t1) (t2≥expansion rate*t1), and a width w2 of the narrow X-ray sensor is less than expansion rate*first width w1/2 (w2<expansion rate*w1/2). In addition the narrow X-ray sensor 311 is installed to move in a rotation trajectory of the sensing unit 31 based on the rotation shaft 25C, for example, in a tangential direction of a circular trajectory, and the generating unit 32 emits an X-ray beam XC toward the narrow X-ray sensor 311 in association with the movement of the narrow X-ray sensor 311.

In the present figure, concentric circles F, FA, FB, and FC based on the rotation shaft 25C are FOVs expanded according to a movement range of the narrow X-ray sensor 311. For example, when the narrow X-ray sensor 311 is in a fixed state at an initial position represented in a solid line and the rotation supporter 30 rotates at a predetermined angle or more, for example 360 degrees, an X-ray CT image of the smallest FOV F may be obtained. The above case is substantially identical to a conventional half beam X-ray CT radiographing apparatus. In addition, during continuous X-ray imaging accompanied with additional rotations based on the rotation shaft 25C, when the narrow X-ray sensor 311 moves from the position represented in a solid line by, for example, a width thereof in a tangential direction, that is to 311A, a FOV FA expands in radius by the width of the narrow X-ray sensor 311. Similarly, during continuous radiographing, when the narrow X-ray sensor 311 moves by twice of the width thereof, or when the narrow X-ray sensor 311 moves by three times of the width thereof, FOVs FB and FC also expand in response to the increase in a range of movement. Accordingly, the width of the narrow X-ray sensor 311 is smaller than a value obtained by multiplying radius of actual expanded FOVs FA, FB, and FC by a maximum expansion rate.

In reference, for a convenience of description, in the above description, movement of the narrow X-ray sensor 311 is performed in stages according to a rotation period based on the rotation shaft 25C. Preferably, the movement of the narrow X-ray sensor 311 may be performed while the rotation based on the rotation shaft 25C is performed. Description thereof will be easily understood by a description below.

In terms of apparatus configuration, the sensing unit 31 includes a narrow X-ray sensor driver 312 moving the narrow X-ray sensor 311 in a tangential direction of a rotation trajectory within a limited range. The narrow X-ray sensor driver 312 may be configured to have, for example, a motor 315 generating driving power, a driving shaft 314 transferring the generated driving power, and a connector 313 connecting a part of the narrow X-ray sensor 311 and the driving shaft 314. However, such a mechanical configuration is merely an example and may be implemented in various forms.

Meanwhile, the generating unit 32 radiates an X-ray beam XC with a width sufficient to cover the width of the narrow X-ray sensor 311 focused in association with the positional movement of the narrow X-ray sensor 311. As a configuration example for the same, the generating unit 32 may include an X-ray generator 321 emitting an X-ray beam XT with a wide width covering the movement range of the narrow X-ray sensor, and a collimator 322 adjusting the X-ray beam XT with the wide width, and emitting an X-ray beam XC with a narrow width covering the width of the narrow X-ray sensor 311 and focused according to the position of the narrow X-ray sensor 311. The collimator 322 may be configured to have at least one blade 323 capable of partially shielding an X-ray beam, a motor 324 generating, for example, driving power for moving the at least one blade 323, a driving shaft 325 transferring the generated driving power, and a connector 326 connecting a part of the 323 and the driving shaft 325. The collimator 322 may drive one blade having a slit with a predetermined width and which passes through the focused X-ray beam XC by using one motor, or may drive at least two blades by using a motor separately provided.

However, such a configuration of the above-mentioned generating unit 32 is merely an example, and may be implemented in various forms. For example, the generating unit 32 may be configured to have an X-ray generator emitting an X-ray beam with a narrow width covering the width of the narrow X-ray sensor 311, and adjusting a radiation direction of the X-ray generator in association with a positional movement of the narrow X-ray sensor 311 so as to emit a focused X-ray beam. Various other configurations are possible.

Meanwhile, the X-ray imaging apparatus according to the embodiment described above may further include the controller 60 connected to the generating unit 32 and the sensing unit 31, and controlling the generating unit 32 to emit an X-ray beam XC focused in association with a positional movement of the narrow X-ray sensor 311. In detail, the controller 60 may be, for example, connected to the narrow X-ray sensor driver 312 and control the motor 315, and control a direction of the X-ray beam emitted from the generating unit 32 by using a control signal of the narrow X-ray sensor driver 312 or a feed-backed signal including positional information of the narrow X-ray sensor 311. Controlling the direction of the X-ray beam may be performed by controlling the motor 324 that drives the collimator 322 as described in the embodiment of the present figure. However, when the generating unit 32 is implemented in a different form as above, a detailed target that receives a control signal of the controller 60 may vary.

The present figure shows the rotation shaft 25C when viewed from above, an inclination in a vertical direction of the sensing unit 31 and the X-ray generator 321 is not shown. However, similarly to the sensing unit 31T and the X-ray generator 321T shown in FIG. 1, the sensing unit 31 and the X-ray generator 321 may be disposed to be inclined relative to the vertical rotation shaft 25C. The above feature is the same in the following description.

Figure 4:
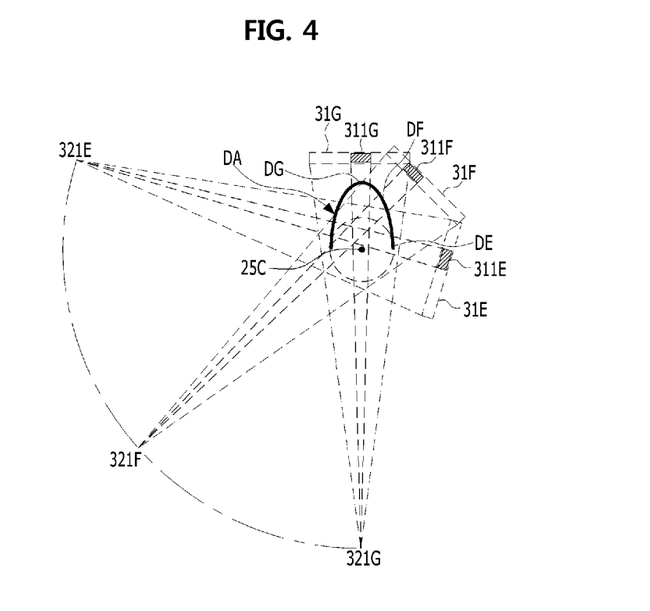
FIG. 4 is a view showing of radiographing a panoramic image according to an arch trajectory by using the radiographing unit according to an embodiment of FIG. 3.

FIG. 4 is a view showing radiographing a panoramic image according to an arch trajectory by using the radiographing unit according to an embodiment of FIG. 3.

As shown in the figure, sensing units 31E, 31F, and 31G including small width sensors 311E, 311F, and 311G rotate based on the rotation shaft 25C, and positions of the small width sensors 311E, 311F, and 311G are moved in a tangential direction of the rotation trajectory, that is, move in a width direction thereof, and thus effect of moving a rotation shaft in a conventional X-ray radiographing apparatus is obtained without actually moving the rotation shaft 25C. Accordingly, the X-ray CT radiographing apparatus according to the present invention may provide an X-ray CT image and a three-dimensional image, and also provide an X-ray panoramic image for image layers distributed along an arch trajectory DA by using the above features.

Herein, since the rotation shaft 25C of the radiographing unit is fixed and the arch trajectory DA has an arrow or arc form rather than a circular form, distances between transmitted images obtained according to positions of the small width sensor 11E, 311F, and 311G shown in the figure, that is, posterior teeth DE, eye teeth DF, or anterior teeth DG, and the small width sensors 311E, 311F, and 311G vary. Distances between the X-ray generators 321E, 321F, and 321G and the small width sensors 311E, 311F, and 311G at the positions thereof are identical, and thus a difference in magnification ratio occurs in the obtained transmitted image. In the example of the present figure, a transmitted image having a relatively low magnification ratio is obtained for the anterior teeth DG, and a transmitted image having a relatively high magnification ratio is obtained for the posterior teeth DE. Accordingly, when the radiographing unit reconstructs a panoramic image for the arch trajectory DA by using the number of transmitted images obtained as above, compensation or correction operations for the magnification ratio is required for obtaining an image to which uniform magnification ratios are applied to respective parts.

Meanwhile, when the X-ray imaging apparatus according to the present embodiment obtains transmitted images of respective parts of the arch shape, for example, the posterior teeth DE, the eye teeth DF, and the anterior teeth DG, the X-ray imaging apparatus may obtain and store geometry information of an angle of the rotation supporter, and positions of the small width sensors 311E, 311F, and 311G in the sensing units 31E, 31F, and 31G, or a value capable of calculating the same. By using the above geometry information and coordinate information of an arch trajectory, a magnification ratio value for each transmitted image may be obtained, or a relation of a magnification ratio according to the position of the obtained transmitted image may be obtained.

Figure 5:
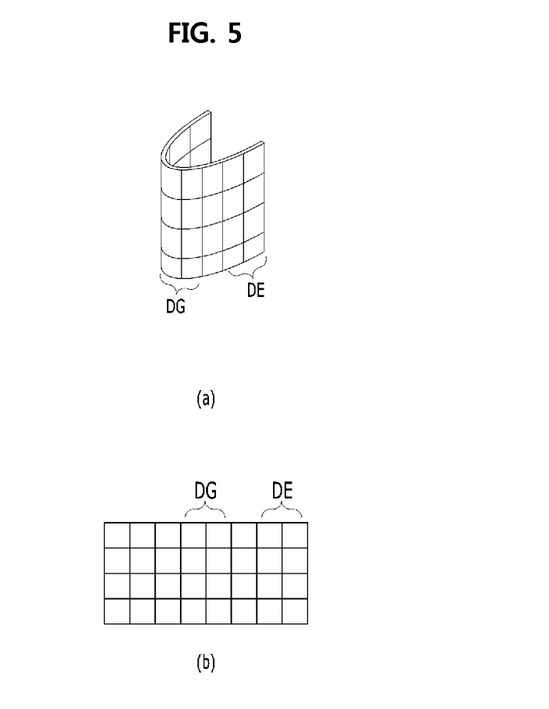
FIG. 5(a) is a perspective view showing an image layer according to an arch trajectory in a grid form, a central part bent as an arrow corresponds to front teeth, that is, anterior teeth DG, and both end part corresponds to molars, that is posterior teeth DE.
FIG. 5(b) shows an optimal panoramic image in which the image layer is shown in planar surface.

FIG. 5 is a schematic diagram showing an optimal relation between image layers according to an arch trajectory and a panoramic image obtained by radiographing the same.

FIG. 5(a) is a perspective view showing an image layer according to an arch trajectory in a grid form, a central part bent as an arrow corresponds to front teeth, that is, anterior teeth DG, and both end part corresponds to molars, that is posterior teeth DE. FIG. 5(b) shows an optimal panoramic image in which the image layer of FIG. 5(a) is shown in planar surface. Herein, the optimal panoramic image means a panoramic image without distortion according to a magnification ratio difference by parts. In FIG. 5(b), there is no difference in magnification ratios of the anterior teeth DG and the posterior teeth DE.

In the X-ray imaging apparatus according to the present invention, in order to obtain a panoramic image without distortion by the above magnification ratio difference, several methods may be used. A first method is, as described above, a method of calculating a magnification ratio of an area of interest of the radiographed subject by using geometry information obtained when obtaining each transmitted image in the radiographing unit, and reconstructing a panoramic image by using a number of transmitted images in which a magnification ratio is reflected. When shifting and overlapping the number of transmitted images in a horizontal axial direction for reconstruction, a shift interval between neighboring transmitted images is identical to an actual distance between areas of interest of the radiographed subject on an arch trajectory.

However, the X-ray imaging apparatus according to the present invention is not limited to the above panoramic image reconstructing method. Magnification ratio correction is performed first for each transmitted image as described above, and a panoramic image without distortion may be obtained when the panoramic image is reconstructed by shifting and overlapping by reflecting an absolute position of the area of interest of the radiographed subject on the arch trajectory. Meanwhile, much of time and many calculation resources are required for image reconstruction operation. In order to solve the above problem and to provide a panoramic image without distortion, another method of compensating or correcting a magnification ratio may be used. Such a method will be described below in detail.

Figure 6:
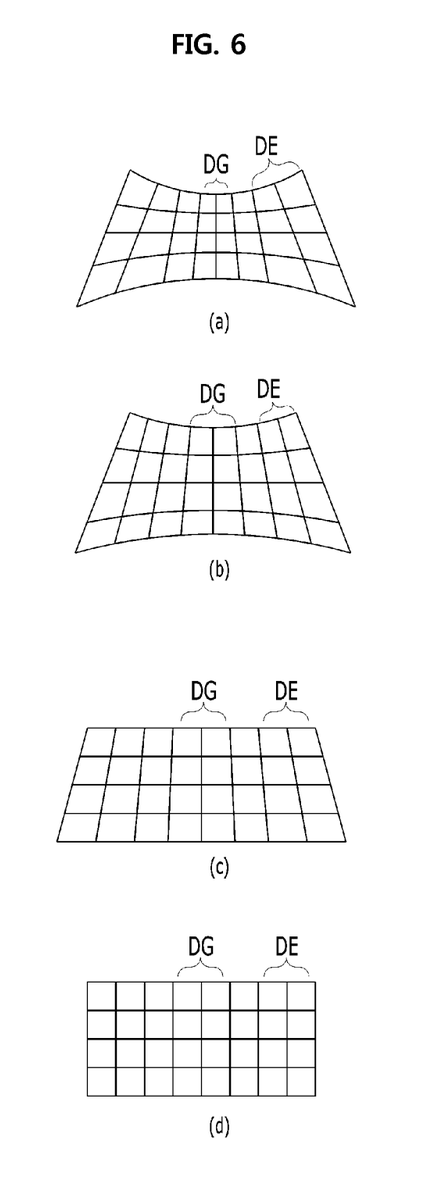
FIG. 6(a) is a view schematically showing an example of a distorted panoramic image using the radiographing unit of the X-ray imaging apparatus without applying compensation or correction in magnification ratio.
FIG. 6(b) is a view schematically showing an example of a panoramic image reconstructed by applying compensation in magnification ratio in a horizontal axial direction of the panoramic imaging sequence described with reference to FIG. 4.
FIG. 6(c) is a view schematically showing a result of performing magnification ratio correction in a longitudinal axial direction for a panoramic image.
FIG. 6(d) is a view schematically showing a result of correcting image distortion in a trapezoid form.

FIG. 6 is a schematic diagram showing distortion of a panoramic image obtained by radiographing an arch shape form of FIG. 5 and a correction method thereof.

FIG. 6(a) is a view schematically showing an example of a distorted panoramic image using the radiographing unit of the X-ray imaging apparatus in which the rotation supporter rotates and the small width sensor simultaneously moves in a width direction thereof, and compensation or correction in magnification ratio is not applied. As described with reference to FIG. 4, the magnification ratio of the anterior teeth DG is relatively low, and the magnification ratio of the posterior teeth DE is relatively large. Accordingly, when a panoramic image is reconstructed without performing compensation or correction in magnification ratio, an image layer of the FIG. 5(a) described above is represented to be, as shown FIG. 6(a), distorted where grid intervals in horizontal axial and longitudinal axial directions of the anterior teeth DG are relatively narrow, and grid intervals in horizontal axial and longitudinal axial directions of the posterior teeth DE are relatively wide.

Image distortion where grid intervals of the posterior teeth DE in horizontal axial direction are more widely distorted than actual grid intervals is related to a method of reconstructing a panoramic image. Generally, when overlapping by sequentially shifting a number of radiographed transmitted images according to a preset radiographing sequence and radiographed in a predetermined rotation speed and a predetermined frame rate, a panoramic image is reconstructed under assumption that shift intervals of the areas of interest of the radiographed subject are distributed on the arch trajectory for each transmitted image frame. The above reconstruction method is suitable for providing a reconstruction image by using relatively small calculation resource and in a short time. However, the method accompanies image distortion as shown in FIG. 6(a).

FIG. 6(b) is a view schematically showing an example of a panoramic image reconstructed by applying compensation in magnification ratio in a horizontal axial direction of the panoramic imaging sequence described with reference to FIG. 4. Herein, compensation in magnification ratio in a horizontal axial direction means that, in order to perform compensation for radiographing sequence distortion described with reference to FIG. 6(a), that is during obtaining a number of transmitted images, a rotation speed of the rotation supporter is changed or a frame rate when obtaining the number of transmitted image frames is changed according to a position of the sensing unit, in more detail, according to a change in distance between areas of interest of the subject and the small width sensor on the arch trajectory.

Describing with reference to FIG. 4, when radiographing the anterior teeth DG, a magnification ratio becomes relatively small since the distance between the arch trajectory and the small width sensor 311G becomes close, and thus a rotation speed of the rotation supporter becomes slow when a frame rate is constant. Alternatively, when the rotation speed is constant, the frame rate, that is, a number of radiographing frames per second is increased so that a transmitted image for a relatively fine arch trajectory is obtained. In a section where a distance between the arch trajectory and the small width sensor 311E becomes as large as the posterior teeth DE so that the magnification ratio is relatively large, a transmitted image is obtained by relatively increasing the rotation speed when the frame rate is constant, or by relatively decreasing the frame rate when the rotation speed is constant. When the number of transmitted image frames obtained as above is shifted and overlapped in a predetermined interval to reconstruct an image, image distortion generated by the magnification ratio difference in a horizontal axial direction described in FIG. 6(a) may be compensated. As a result, in FIG. 6(b), grid intervals are constant in a horizontal axial direction. Meanwhile, operation of compensation in magnification ratio accompanied with changes in a rotation speed of the rotation supporter or in a frame rate of the sensing unit may be performed by the controller 60 of FIG. 3.

FIG. 6(c) is a view schematically showing a result in which magnification ratio correction in a longitudinal axial direction is performed for a panoramic image in which magnification ratio compensation in a horizontal axial direction is performed as the method of FIG. 6(b). The magnification ratio correction in a longitudinal axial direction is performed by calculating a magnification ratio in a longitudinal axial direction which is different according to a position in a horizontal axial direction on an arch trajectory by using geometry information obtained when performing a radiographing sequence as described above, and by correcting the magnification ratio in a longitudinal axial direction by reflecting the calculated magnification ratio in a part corresponding to the image of FIG. 6(b). As a result, in FIG. 6(c), grid intervals in a longitudinal axial direction are corrected to be identical in the anterior teeth DG and the posterior teeth DE.

Meanwhile, as described above, the X-ray imaging apparatus according to an embodiment of the present invention includes the sensing unit 31T installed to be inclined to a direction of the rotation shaft 25C of the rotation supporter as shown in FIG. 1. Herein, as described with reference to FIG. 2, image distortion occurs due to a difference between upper and low magnification ratios, accordingly, image distortion in a trapezoid form is shown in an image of FIG. 6(c).

FIG. 6(d) is a view schematically showing a result where image distortion in a trapezoid form due to tilting of the sensing unit is corrected. As shown in FIG. 2, magnification ratio distribution according to height of the sensing unit 31T is geometrically calculated, and image distortion due to tilting of the sensing unit may be corrected by reflecting the calculated magnification ratio distribution in a panoramic image corresponding to FIG. 6(c).

Herein, correction described with reference to FIGS. 6(c) and 6(d) may be sequentially or simultaneously performed when reconstructing a panoramic image in the reconstructing unit by using the number of transmitted images. When both of magnification ratio corrections described above are perform at the same time, a panoramic image of an intermediate step corresponding to FIG. 6(b) may be divided into a number of areas, a correction constant in a horizontal axial direction and a correction constant in a longitudinal axial direction may be calculated for each area in advance, and a corrected panoramic image corresponding to FIG. 6(d) may be provided by applying the calculated constants.

Figure 7A:
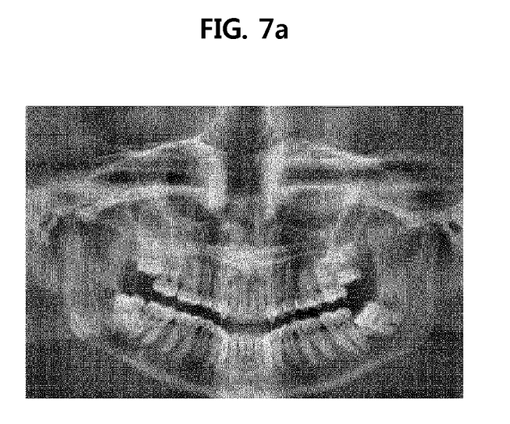
FIG. 7a is a view showing an example of non-corrected panoramic image to which expansion compensation is not applied.

FIG. 7a is a view showing an example of non-corrected panoramic image to which magnification ratio compensation is not applied. In horizontal axial and longitudinal axial directions, anterior teeth are distorted to be relatively small, and posterior teeth are distorted to be relatively large.

Figure 7B:
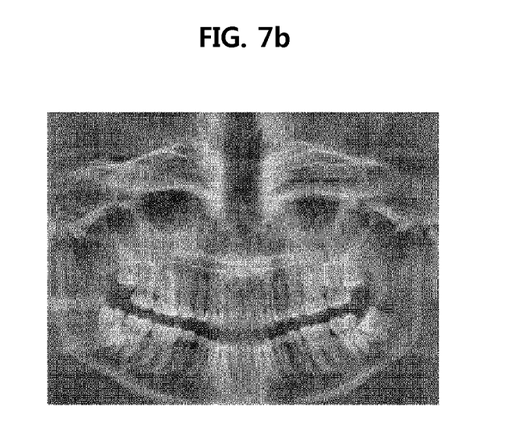
FIG. 7b is a view showing an example of a panoramic image in which horizontal axial magnification ratio compensation is applied to a radiographing sequence

FIG. 7b is a view showing an example of a panoramic image in which horizontal axial magnification ratio compensation is applied to a radiographing sequence. Teeth in anterior teeth and posterior teeth in a horizontal axial direction are corrected to be closer than actual tooth width.

Figure 7C:
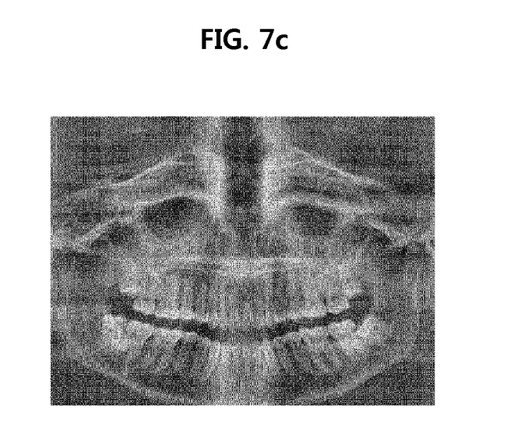
FIG. 7c is a view showing an example of a panoramic image in which longitudinal axial magnification ratio correction and tilting correction are applied to a radiographing sequence of the image of FIG. 7b.

FIG. 7c is a view showing an example of a panoramic image in which longitudinal axial magnification ratio correction and tilting correction are applied to the radiographing sequence of the image of FIG. 7b. Herein, magnification ratio distortion in a longitudinal axial direction and image distortion according to the magnification ratios difference in upper and low parts of the image are corrected.

INDUSTRIAL APPLICABILITY

The present invention relates to an X-ray imaging apparatus, and may be used for a medical X-ray image diagnosing apparatus, more particularly, may be used in the field of a dental X-ray diagnosing apparatus.

The invention claimed is:

1. An X-ray imaging apparatus, the apparatus comprising:
a rotation supporter rotating based on a rotation shaft;
a generating unit disposed in a first side of the rotation supporter and including an X-ray generator radiating an X-ray beam;
an X-ray sensor disposed in a second side of the rotation supporter to face to the generating unit with a subject in between; and
a controller changing a rotation speed of the rotation supporter or a frame rate of the X-ray sensor according to a change in distance between an area of interest of the subject and the sensor when performing an X-ray imaging sequence obtaining a number of frame images by rotating the rotation supporter,
wherein the controller compensates a change in magnification ratio by changing the rotation speed of the rotation supporter or the frame rate of the X-ray sensor according to the change in the distance between an area of interest of the subject and the X-ray sensor.

2. The apparatus of claim 1, wherein the controller relatively increases the rotation speed of the rotation supporter or relatively decreases the frame rate of the X-ray sensor in a section where the magnification ratio is relatively large.

3. The apparatus of claim 2, wherein the controller maintains the rotation speed of the rotation supporter to be constant, and relatively decreases the frame rate of the X-ray sensor in a section wherein the magnification ratio is relatively large.

4. The apparatus of claim 2, wherein the controller maintains the frame rate of the X-ray sensor to be constant, and relatively increases the rotation speed of the rotation supporter in a section where the magnification ratio is relatively large.

5. The apparatus of claim 1, wherein the X-ray imaging sequence is a panoramic imaging sequence, and an area of interest of the subject is distributed along an arch trajectory.

6. The apparatus of claim 5, wherein the controller relatively increases the rotation speed of the rotation supporter or relatively decreases the frame rate of the X-ray sensor in a section for obtaining a frame image of posterior teeth than in a section for obtaining a frame image of anterior teeth.

7. The apparatus of claim 5, further comprising an image reconstructing unit shifting and overlapping the number of frame images in a predetermined interval to compensate a magnification ratio difference in a horizontal axial direction according to a position on the arch trajectory, and correcting a magnification ratio in a longitudinal axial direction by applying ratios different from each other according to a position in a horizontal axial direction on the arch trajectory.

8. An X-ray imaging apparatus, the apparatus comprising:
a rotation supporter rotating based on a rotation shaft;
a generating unit disposed in a first side of the rotation supporter and including an X-ray generator radiating an X-ray beam;
an X-ray sensor disposed in a second side of the rotation supporter to face the generating unit with a subject in between; and
a controller changing a rotation speed of the rotation supporter or a frame rate of the X-ray sensor according to a change in distance between an area of interest of the subject and the X-ray sensor to compensate a change in magnification ratio when performing an X-ray imaging sequence obtaining a number of frame images by rotating the rotation supporter,
wherein the X-ray generator is installed such that a direction of the X-ray beam has a predetermined slope relative to a surface perpendicular to the rotation shaft, and the X-ray sensor is installed to be inclined at a predetermined angle relative to a surface parallel to the rotation shaft,
wherein the X-ray imaging sequence is a panoramic imaging sequence, and the area of interest of the subject is distributed along an arch trajectory, and the apparatus further comprises an image reconstructing unit compensating a magnification ratio difference in a horizontal axial direction according to a position on the arch trajectory by shifting and overlapping the number of frame images in a predetermined interval, and correcting a magnification ratio in a longitudinal axial direction by applying ratios different from each other according to a position in a horizontal axial direction on the arch trajectory.

9. The apparatus of claim 8, wherein the image reconstructing unit corrects upper and low magnification ratio differences due to tilting of the X-ray sensor.

* * * * *